United States Patent [19]

Grahn et al.

[11] Patent Number: 5,378,459
[45] Date of Patent: Jan. 3, 1995

[54] PHARMACEUTICAL PREPARATION IN THE TREATMENT OF TONSILLITIS

[76] Inventors: Eva E. Grahn, Bondegatan 32, S-902 54; Stig E. F. Holm, Gimonäsvägen 25, S-902 40, both of Umea, Sweden

[21] Appl. No.: 194,753

[22] Filed: Feb. 10, 1994

Related U.S. Application Data

[63] Continuation of Ser. No. 478,683, Feb. 12, 1990, abandoned.

[30] Foreign Application Priority Data

Feb. 15, 1989 [SE]  Sweden ................... 8900510

[51] Int. Cl.⁶ .................. A61K 35/74; C12N 1/20
[52] U.S. Cl. ................... 424/93.44; 435/885; 424/50
[58] Field of Search ............. 424/93 H, 50; 435/885

[56] References Cited

U.S. PATENT DOCUMENTS 4,454,109  6/1984  Hillman .................. 424/50
4,797,278  1/1989  Kawai et al. ............. 424/93

FOREIGN PATENT DOCUMENTS 0058575  8/1982  European Pat. Off. .

OTHER PUBLICATIONS

Holm et al, Biol. Abstracts, vol. 57 (1974) No. 41956.
Dajani et al, Antimicrob. Agents Chemotherap. vol. 9 (1976) pp. 81–88.
Pediatr.Res., vol. 14, 1980 Katherine Sprunt, MD et al: "Abnormal Colonization of Neonates in an ICU: Conversion to Normal Colonization of Neonates by Pharyngeal Implantation of Alpha Hemolytic Streptococcus Strain 215", see page 308–313.
Bacteriological Reviews, vol., 1976 John R. Tagg et al: "Bacteriocins of Gram-Positive Bacteria", see pp. 722–756.
Grahn et al., I Zbl.Bakt.Hyg.A 256:72–79 (1983).
Grahn et al., I Zb;.Bakt.Hyg.A 254:459–469 (1983).
Sprunt et al., Pediatr. Res. 14:308–313 (1980).
Roos et al., Clin. Microbiol. Infect. Dis. 8: (1989).
Tagg et al, Bacteriological Reviews 40:722–756 (1976).
Holm et al., Biol. Abs. 57:41956 (1974).
Dajani et al., Antimicrob. Agents Chemother. 9:81–88 (1976).
Holm et al., Scand J Infect Dis, Suppl. 39:73–78 (1983).

*Primary Examiner*—Jacqueline Stone
*Attorney, Agent, or Firm*—White & Case

[57] ABSTRACT

A pharmaceutical preparation in the prophylaxis against and/or the treatment of β-streptococcal tonsillitis is described. The preparation includes at least one viable microorganism strain selected from the group consisting of *Streptococcus sanguis II* strains with the deposit numbers NCIB 40104, NCIB 40105 and NCIB 40106, the *Streptococcus mitis* strain with the deposit number NCIB 40107 and streptococci strains with essentially the same capacity to inhibit β-streptococci as the deposited strains, in a pharmaceutically acceptable medium wherein the microorganisms retain their viability. Use of the preparation in the prophylaxis against and/or the treatment of β-streptococcal tonsillitis is also described.

7 Claims, No Drawings

PHARMACEUTICAL PREPARATION IN THE TREATMENT OF TONSILLITIS

This application is a continuation of application Ser. No. 07/478,683, filed Feb. 12, 1990 now abandoned.

The present invention refers to a pharmaceutical preparation in the prophylaxis against and/or the treatment of β-streptococci tonsillitis.

BACKGROUND

Tonsillitis, that is inflammation of the tonsils, is a wide-spread health problem. It is estimated that in Sweden approximately 300 000 people are affected each year by acute tonsillitis. About 30–50% of these cases are caused by β-streptococci. Tonsillitis is usually treated with penicillin, e g phenoxymethyl penicillin, but in about 10–25% of the cases the treatment is ineffective, and the patient is affected by recurrent tonsillitis. Tonsillitis is particularly common at day care centers, in schools and also within families, where people are in close contact with each other and several chances of infection occur. The consequences are recurrent medical treatment, sick reportings and penicillin treatment, which are not only a great health problem but also an economical problem.

The reasons for the relatively high frequency of ineffective treatments are supposed to depend on, apart from local deficiencies in the immuno defence of the patient and general immunological deficiencies, inadequate antibiotic activity ,At the site of infection. The latter includes such factors as the compliance of the patient to the medication, the particular dosage of the penicillin, the number of doses and impaired absorption of the drug. Also inactivation of penicillin by β-lactamase producing bacteria, resulting in an insufficient penicillin concentration at the focus of infection has been mentioned. Other factors connected with ineffective treatments of β-streptococcal tonsillitis is disturbancies of the normal flora resulting in an increased susceptibility to streptococcal infections and penicillin tolerance of the group A β-streptococci.

It is known that bacterial interference among the bacteria of the throat flora may play an important role at tonsillitis. It has been demonstrated that certain strains of streptococci inhibit the growth of ordinary infection producing β-streptococci. This applies particularly to certain α-streptococci. People with the above mentioned recurrent infections are often lacking inhibiting α-streptococci in their normal throat flora, while people having these α-streptococci seldom are afflicted with tonsillitis.

Sanders et al. (Sanders, C., Nelsen, G., Sanders, E.: Bacterial interference, II. Epidemiological determinants of the antagonistic activity of the normal throat flora against group A streptococci. Infection and Imminity 1977, 16:599–603) have demonstrated that certain strains of Streptococcus viridans inhibit the growth of group A streptococci (GAS). Sanders also demonstrated an inhibiting effect of normally occurring α-streptococci against GAS in infected children.

The protective role in the throat of α-streptococci against β-streptoccocal infections has also been shown by Grahn and Holm (Grahn, E., Holm, S. E.: Bacterial interference in the throat flora during a streptococcal tonsillitis outbreak in an apartment house area. Zentralblatt fe,uml/u/ r Bakteriologie Mikrobiologie und Hygiene A 1983, 256:72–79) and Roos et al. (Roos, K., Grahn, E., Holm, S. E.: Evaluations of betalactamase activity and microbial interference in treatment failures of acute streptococcal tonsilitis. Scandinavian Journal of Infectious Diseases 1986, 18:313–19). They have elucidated that the lack of interfering α-streptococci is one of the main reasons of the often ineffective treatment of streptococcal tonsillitis.

Further, Beck (Interference by an α-hemolytic streptococcus of β-hemolytic pathogenic streptococci, Inflammation, 3:463–465, 1979) has found a strain of Streptococcus viridans with a high inhibiting capacity against GAS and he has suggested "implantation" of this strain in people with recurrent streptococcal tonsillitis. A similar report has previously been presented by Sprunt et al. (Sprunt K., Leidy G., Redman W.: Abnormal colonisation of neonates in an ICU: Conversion to normal colonisation by pharyngeal implantation of alpha-hemolytic streptococcus strain 215. Pediatr Res 14:308–313, 1980), who implanted a strain of α-streptococci in the nasopharynx of 22 children apprehended to be in danger of infection. The implantation turned out to be successful in 16 of the children and caused a change to the normal flora in 7 of the children to the effect that the implanted strain was the sole strain of α-streptococci to be found 4–18 days after the implantation.

The bacteria in the normal flora inhibit invading bacteria in different ways, and the factors behind are e g competition for important growth factors, pH-variations, accumulation of waste products, formation of peroxide, bacterial toxins and enzymes, and also production of substances known as bacteriocins. The known bacteriocins are very similar to antibiotics, but differ in having a very selective effect and do not disturb the very important anaerobic bacterial flora. The inhibiting effect of the α-streptococci on the α-streptococci has been shown to depend in a high degree on the presence of bacteriocins produced by α-streptococci. There exists a need for an effective pharmaceutical preparation in the prophylaxis against and treatment of β-streptococcal tonsillitis.

DESCRIPTION OF THE INVENTION

In one aspect of the invention there is provided a pharmaceutical preparation in the prophylaxis against and/or treatment of β-streptococcal tonsillitis, which preparation is characterized in comprising at least one viable microorganism strain selected from the group consisting of Streptococcus sanguis II strains with the deposit numbers NCIB 40104, NCIB 40105 and NCIB 40106, the Streptococcus mitis strain with the deposit number NCIB 40107 and streptococcus strains with essentially the same capacity for inhibiting β-streptococci as the deposited strains, in a pharmaceutically acceptable medium in which the microorganisms retain their viability.

In another aspect of the present invention the above mentioned preparation is used in the prophylaxis against and/or the treatment of tonsillitis, possibly after a course of penicillin. Other characteristics of the invention are evident from the following claims.

In a further aspect of the invention there is provided a process for the manufacture of the above mentioned preparation.

The pharmaceutical preparation according to the present invention has been found to be particularly effective in the prophylaxis against and treatment of β-streptococcal tonsillitis. In the experiments described below the preparation according to the invention in a preferred embodiment wherein all the four different strains of α-streptococci are present simultaneously, has been found to eliminate 95–98% of β-streptococci isolated in 3 places in Sweden. Combinations of different numbers of the mentioned microorganism strains are effective as well, but the definitely best effect that has so far been obtained is when all four strains are present. Particularly the strain NCIB 40104 is very effective alone, whereas the remaining 3 strains are separately not as effective as NCIB 40104.

The pharmaceutically acceptable medium consists preferably of NaCl skim milk or Nutramigen ® (registered trade mark Mar. 13, 1981, Re. No. 175 669, proprietor Mead Johnson & Company, Evansville, Ind. USA), but also other pharmaceutically acceptable media in which the viability of the microorganisms are retained, can be used. In one embodiment of the invention physiological saline buffer solution designed to give an isoton composition with a neutral pH is used.

Each one of the microorganisms in the preparation is present in a concentration in said medium of $10^4$–$10^{10}$ CFU/ml (colony-forming units/ml), preferably $10^5$–$10^9$ CFU/ml.

Counterparts to the four strains of microorganisms, of which three belong to the genus *Streptococcus sanguis II* (henceforward called α89a, α502 and α505) and the fourth genus *Streptococcus mitis* (henceforward called α7213) are found in the normal throat flora of most people. The strain α89a corresponds to NCIB 40104 and the strains α502, α505 and α7213 correspond to NCIB 40105, NCIB 40106 and NCIB 40107, respectively.

The Microorganisms According to the Invention

The 4 above mentioned strains in the preparation according to the invention were isolated according to the following procedure. From each Df about 200 people were isolated 5 strains of α-streptococci with different colony appearance, that is about 1000 strains totally. These strains were tested against different types of β-streptococci in vitro in the following way.

All the strains of α-streptococci were first grown in TY-broth, washed and diluted to an optical density of 0.3 at 500 nm (Viatron). This corresponded to $10^4$–$10^5$ CFU/ml. Minidrops of these strains (containing 10–100 CFU) were transferred to blood agar plates (25 strains on each plate) by a Steer's pin replicator (see Steers E., Foltz E. L., Graves B. S., Riden J.: An inocula replicating apparatus for routine testing of bacterial susceptibility to antibiotics. Antibiot Chemother 9:307–311, 1959) and were allowed to dry for 10–15 minutes. The agar plates used in this experiment were made of BBL Colombia Agar Base (Div. Becton Dickinson & Co., Cockeysville, Md. 21030, USA) with 5% steril defibrinated horse blood. The pH was 7.49–7.57.

Different strains of β-streptococci were promptly applied adjacent to each of the α-streptococci strains and the plates were incubated in 5% $CO_2$ at 37° C. Some plates were incubated under anaerobic conditions in order to eliminate peroxide production. Thereafter the inhibiting effect of the α-strains on the β-streptococci was recorded by studying the particular growth inhibiting patterns, which could be read on the agar plates.

The best inhibiting strains were further investigated in different combinations with regard to β-streptococci interference and the four most effective were selected. These four strains, that is α89a, α502, α505 and α7213, were then cultivated separately in TY-broth containing 0.2% glucos at 37° C. over night, washed and suspended in brine. The four selected strains were then tested against 100 different strains of β-streptococci from Umeå, Uppsala and Gothenburg, and 8%, 92% and 89%, respectively of these strains were inhibited.

The four strains of microorganisms in the preparation according to the invention can, suspended in the pharmaceutically acceptable medium, be frozen to −20° C. or be freeze-dryed in order to be preserved. By administration to a patient a pump spray can is suitably used, by which the thawed, liquid preparation can be administered orally and/or nasally.

In one embodiment of the invention the spray can contains a suspension of β-streptococci $10^9$ CFU/ml in 5 ml of physiological saline solution. Each spray dose provides $10^7$ CFU corresponding to about 0.01 ml.

The microorganism strains in the preparation according to the invention are deposited with the National Collection of Industrial & Marine Bacteria Ltd (NCIMB), Torry Research Station, PO Box 31, 135 Abbey Road, Aberdeen AB9 8DG, Great Britain, on the 3rd of Feb. 1989, and have the deposit numbers NCIB 40104, NCIB 40105, NCIB 40106 and NCIB 40107. The mentioned organism strains are interpreted or classified according to the API 20 system (API-system—La Balme les Grottes—38390 Montalieu—Vercieu, France). The interpretation table and the results of the interpretation are presented on the following pages.

INTERPRETATION TABLE

| TESTS | SUBSTRATES | REACTIONS/ ENZYMES | RESULTS NEGATIVE | RESULTS POSITIVE |
|---|---|---|---|---|
| VP | Pyruvate | Acetoin Production | VP 1 + VP 2/wait to 10 min Colourless | Pink-red |
| HIP | Hippurate | Hydrolysis | NIN/wait to 10 min Colourless/Pale blue 4 hrs    24 hrs | Dark blue/Violet 4 hrs    24 hr |
| ESC | Esculin | β-glucosidase | Colourless    Colourless Pale yellow    Pale yellow               Light grey | Grey    Black Black |
| PYRA | Pyrrolidonyl 2 naphtylamide | Pyrrolidonylarylamidase | ZYM A + ZYM β/10 min (1) if necessary, decolorize with intense light Colourless or very pale orange | Orange |
| αGAL | 6-Bromp-2-naphtyl α-D-Galactopyranoside | α-galdctosidase | Colourless | Violet |
| βGUR | Naphthol AS-BI β-D-glucuronate | β-glucuronidase | Colourless | Blue |
| βGAL | 2-naphthyl-β-D | β-galactosidase | Colourless or very | Violet |

-continued

INTERPRETATION TABLE

| TESTS | SUBSTRATES | REACTIONS/ ENZYMES | RESULTS NEGATIVE | RESULTS POSITIVE |
|---|---|---|---|---|
| PAL | galactopyrdnoside 2-naphthyl phosphate | Alkaline Phosphatase | pale violet Colourless or very pale violet | Violet |
| LAP | L-leucine-2-naphthyl amide | Leucine arylamidase | Colourless | ZYM A + ZYM $\beta$/10 min (1) if necessary, decolorize with intense light Orange |
| ADH | Arginine | Arginine dihydrolase | Yellow | Red |

| | | | 4 hrs | 24 hrs | 4 hrs | 24 hr |
|---|---|---|---|---|---|---|
| RTB | Ribose | Acidification | Red | Orange/Red | Orange/Yellow | Yellow |
| ARA | L-Arabinose | Acidification | Red | Orange/Red | Orange/Yetlow | Yellow |
| MAN | Mannitol | Acidification | Red | Orange/Red | Orange/Yellow | Yellow |
| SOR | Sorbitol | Acidification | Red | Orange/Red | Orange/Yellow | Yellow |
| LAC | Lactose | Acidification | Red | Orange/Red | Orange/Yellow | Yellow |
| TRE | Trehalose | Acidification | Red | Orange/Red | Orange/Yellow | Yellow |
| INU | Inulin | Acidification | Red | Orange/Red | Orange/Yellow | Yellow |
| RAF | Raffinose | Acidification | Red | Orange/Red | Orange/Yellow | Yellow |
| AMD | Starch (2) | Acidification | Red | Orange/Red | Orange/Yellow | Yellow |
| GLYG | Glycogen | Acidification | Red or orange | | Bright yellow | |

(1) During a second reading after 24 hours of incubation, a deposit may be noticed in the tubes where the reagents ZYM A and ZYM B have been added. This phenomenon is normal and should not be taken into consideration.
(2) The acidification of starch is frequently weaker than that of othersugars.

RESULT OBTAINED AT INTERPRETATION OF STREPTOCOCCUS STRAINS

| Test | $\alpha$89a | $\alpha$502 | $\alpha$505 | $\alpha$7213 | |
|---|---|---|---|---|---|
| VP | − | − | − | − | |
| HIP | − | − | − | − | |
| ESC | − | − | − | − | |
| PYRA | − | − | − | − | |
| $\alpha$GAL | + | + | + | − | |
| $\beta$GUR | − | − | − | − | |
| $\beta$GAL | − | − | − | − | |
| PAL | + | + | + | + | |
| LAP | + | + | + | + | |
| ADH | + | + | + | + | |
| RIB | − | − | − | − | |
| ARA | − | − | − | − | |
| MAN | − | − | − | − | |
| SOR | − | − | − | − | |
| LAC | + | + | + | + | |
| TRE | (+) | − | − | − | + |
| INU | − | − | − | − | |
| RAF | + | + | + | − | |
| AMD | + | + | + | + | |
| GLYG | − | − | − | − | |
| hemolysis | − | − | − | − | all have $\alpha$—hemolysis (green hemo—lysis) |
| | S. sanguis II | S. sanguis II | S. sanguis II | S. mitis | |

Experiments

The object of the following experiments was to recolonize patients with recurrent tonsillitis by using a preparation according to the invention containing the four α-streptoccocal strains, which preparation inhibits the GAS of the patients, and analyze the protective ability against recurrent GAS tonsillitis of the new flora.

Family A (parents and three children) had experienced 25 acute tonsillitis during the last 3.5 months of 1986. Repeated cultivations of throat samples had revealed the presence of the β-streptoccus GAS T-type 12 from all members of the family. They had been given alternatively phenoxymethyl penicillin (12.5 mg/kg of bodyweight twice a day for 10 days) and erythromycin (20 mg/kg of bodyweight twice a day for 10 days), but only a temporary improvement occurred.

Family B (parents and two children) had experienced 11 acute streptococcal tonsillitis (GAS T-type 12) during the last 3 months of 1986. As in the case of family A all family members were treated with phenoxymethyl penicillin and erythromycin. Certain β-streptococcal isolates from family B were resistant against erythromycin [MIC (minimum inhibitory concentration) greater than 8 mg/l]. The occurrence of streptococcal tonsillitis with the two families are given in table 1.

The isolated α-streptococci from the totally nine patients of the two families all lacked growth inhibiting capacity against their own GAS. The method used to demonstrate growth inhibition, that is bacterial interference, against GAS has been described by Grahn et al. (Grahn, E., Holm, S. E., Roos, K., Ekedahl, C.: Interference of alfa-haemolytic streptococci isolated from tonsillar surface, on beta-haemolytic streptococci, *Streptococcus pyogenes*—methodological study. Zentralblatt für Bakteriologie Mikrobiologie und Hygiene A 1983, 254:459-468).

In Feb. 1987 all members of the two families were treated with the preparation according to the present invention. The preparation in an amount of about $10^7$ CFU/ml for each of the 4 α-streptococci in the pharmaceutically acceptable medium was sprayed through the nose to the epipharynx and through the mouth to the pharyngotonsillar region of the nine patients. This process was repeated once a day for four days, then once a week for a month, and then once a month for two/three further months. The patients were controlled by cultivating throat samples repeatedly during 8 months from the start of the treatment. At the start of the recolonization with the selected α-streptococci of the preparation according to the invention all nine patients were lacking interfering α-streptococci against their own GAS. In family A all members were carrier of GAS prior to treatment, while on the other hand none in family B was carrier of GAS. None of either family A or B showed any clinical signs of infection. Four months after the last period of treatment only one patient was still carrier of the original GAS strain, and this individual lacked inhibiting α-streptococci as well. In all the remaining patients a heavy growth of the administered α-streptococci was found. This growth was confirmed by the typical growth inhibiting pattern towards different GAS strains and by their biochemical reactions. As can be seen in table 2, which shows the frequency of treatment and microbial results after administration of the GAS inhibiting α-streptococci, the children of family B were exposed to GAS at their day care center and were carrier of said bacteria, but were not affected by infection. The parents of the same family were during the same period not even carrier.

Table 3 shows the occurrence of streptococcal tonsillitis before and after recolonization with α-streptococci. After recolonization with the GAS inhibiting α-streptococci and during a follow up period of eight months none of the patients of the two families showed clinical signs of streptococcal tonsillitis. It is true that some of the family members during this time were carriers of GAS but none was affected with tonsillitis.

As this experiment demonstrates the preparation according to this invention can very successfully be used both in the prophylaxis against and in the treatment of streptococcal tonsillitis. Said preparation can be used concurrently with the termination of an optimally dosed penicillin course in the case where a very powerful and effective treatment of tonsillitis is required.

TABLE 1

| | Sex/Age | Occurence of *Streptococcal tonsillitis*. M stands for male sex and F for female sex. | | | | | | | |
|---|---|---|---|---|---|---|---|---|---|
| | | june 1986 | july | august | sept | oct | nov | dec | jan |
| Family A | M 30 | | | | | * | * | * | * |
| | F 27 | * | * | | * | * | * * | * | * |
| | M 7 | | | * | | * | * | * | * |
| | M 4 | * | | * | * | | * | * | * |
| | F 1 | | * | * | | * | * | * | * |
| Family B | M 36 | | | | | | | * | |
| | F 33 | | | * * | | | * | | * * |
| | M 4 | | | | | | | * | |
| | F 1 | | | | * | * | | | * * |

TABLE 2

| | Sex/Age | Incidence of microbiological results following administration of the preparation according to the invention containing GAS inhibiting α-streptococci. + denotes the presence of GAS | | | | |
|---|---|---|---|---|---|---|
| | | febr | mar 1987 | apr | may-sept | |
| Family A | M 30 | +++ | +− | −− | − | − |
| | F 27 | +++ | −− | −+ | − | − |
| | M 7 | +−− | −− | −− | − | − |
| | M 4 | ++− | −− | − | − | − |
| | F 1 | +++ | −− | − | − | − |
| Family B | M 36 | −−− | −− | −− | − | − |
| | F 33 | −−− | −− | −− | − | − |
| | M 4 | −−− | ++ | − | + | + |
| | F 1 | −−− | ++ | + + | − | − |

TABLE 3

| | Sex/Age | The incidence of β-*Streptococcal tonsillitis* before and after re-colonization with the α-streptococci in the preparation according to the present invention. | | | | | | | | |
|---|---|---|---|---|---|---|---|---|---|---|
| | | Before re-colonization | | | | | | | | After re-colonization |
| | | june 1986 | july | aug | sept | oct | nov | dec | jan | feb-oct 1987 |
| Family A | M 30 | | | | | * | * | * | * | |
| | F 27 | | | * | | * | * | * * | * | |
| | M 7 | | * | * | | * | * | * | * | |
| | M 4 | * | | * | * | | * | * | * | |
| | F 1 | | * | * | | * | * | * | * | |
| Family B | M 36 | | | | | | | * | | |
| | F 33 | | | * * | | | * | | * | |
| | M 4 | | | | | | | * | | |
| | F 1 | | | | * | * | | | * | * |

We claim:

1. A pharmaceutical preparation useful in the prevention or treatment of β-streptococcal tonsillitis, comprising at least one viable microorganism strain selected from the group consisting of *Streptococcus sanguis* II strains with the deposit numbers NCIB 40104, NCIB 40105 and NCIB 40106, and the *Streptococcus mitis* strain with the deposit number NCIB 40107, in a pharmaceutically acceptable medium wherein the microorganisms retain their viability.

2. A pharmaceutical preparation according to claim 1, characterized therein that each streptococcal strain in the preparation is present in a concentration of $10^4$–$10^{10}$ CFU/ml.

3. A pharmaceutical preparation according to claim 1 or 2, characterized therein that the pharmaceutically acceptable medium is NaCl, skim milk or an iron fortified protein hydrolysate formula.

4. A pharmaceutical preparation according claim 1 or 2, which is in the form of a spray for nasal or oral administration.

5. A pharmaceutical preparation according to claim 1 or 2 further comprising all four microorganism strains.

6. A method for using a pharmaceutical preparation in the prevention or treatment of $\beta$-streptococcal tonsillitis comprising the administration of at least one viable microorganism strain selected from the group consisting of *Streptococcus sanguis* II strains with the deposit numbers NCIB 40104, NCIB 40105 and NCIB 40106, and the *Streptococcus mitis* strain with the deposit number NCIB 40107, in the pharmaceutically acceptable medium wherein the microorganism retain their viability.

7. A method according to claim 6, wherein prevention or treatment takes place at the end of a penicillin course.

* * * * *